US007863007B2

(12) United States Patent
Voroteliak

(10) Patent No.: US 7,863,007 B2
(45) Date of Patent: Jan. 4, 2011

(54) MARKER FOR PROLONGED RUPTURE OF MEMBRANES

(75) Inventor: Victor Voroteliak, Brisbane (AU)

(73) Assignee: Swiss Asian Property Limited, Sheung Wan (HK)

( * ) Notice: Subject to any disclaimer, the term of this patent is extended or adjusted under 35 U.S.C. 154(b) by 0 days.

(21) Appl. No.: 12/066,969

(22) PCT Filed: Sep. 15, 2006

(86) PCT No.: PCT/AU2006/001358

§ 371 (c)(1),
(2), (4) Date: Nov. 5, 2008

(87) PCT Pub. No.: WO2007/030890

PCT Pub. Date: Mar. 22, 2007

(65) Prior Publication Data

US 2009/0068692 A1    Mar. 12, 2009

Related U.S. Application Data

(60) Provisional application No. 60/717,683, filed on Sep. 15, 2005.

(51) Int. Cl.
*G01N 33/53* (2006.01)
(52) U.S. Cl. .................. 435/7.1; 436/518
(58) Field of Classification Search ............ None
See application file for complete search history.

(56) References Cited

U.S. PATENT DOCUMENTS 5,783,396 A * 7/1998 Voroteliak et al. ......... 435/7.1

5,891,722 A * 4/1999 Fuks et al. .................. 435/346

FOREIGN PATENT DOCUMENTS

WO    WO92/10585    6/1992
WO    WO 94/21687   9/1994

OTHER PUBLICATIONS

Caughey et al. Reviews in Obstetrics & Gynecology 2008, vol. 1, p. 11-22.*
Drohse et al. (Clinica Chimica Acta 1998 vol. 276, p. 109-120).*
Michel et al., "Proteome analysis of human plasma and amniotic fluid byOff-Gel isoelectric focusing followed by nano-LCMS/MS," *Electrophoresis*, Mar. 2006, pp. 1169-1181, vol. 27, No. 5-6.
Thadikkaran et al., "The role of proteomics in the assessment of premature rupture of fetal membranes," *Clinica Chimica Acta*, Oct. 2005, pp. 27-36, vol. 360.
Guibourdenche, et al., "Rapid detection of insulin-like growth factor-binding protein-1 and foetal fibronectin in cervivo-vaginal secretions to diagnose premature membrane rupture," *Annals of Clinical Biochemistry*, 1999, pp. 388-390, vol. 37, No. 3.
Gaucherand, et al., "Comparative study of three amniotic fluid markers in premature rupture of membranes: fetal fibronectic, alpha-fetoprotein, diamino-oxydase." *Acta Obstetricia et Gynecologica Scandinavica*, Feb. 1995, pp. 118-121, vol. 74, No. 2.
Vuadens, et al., "Identification of biologic markers of the premature rupture of fetal membranes: Proteomic approach," Proteomics, 2003, pp. 1521-1525, vol. 3.

* cited by examiner

*Primary Examiner*—Jacob Cheu
(74) *Attorney, Agent, or Firm*—Alston & Bird LLP

(57) ABSTRACT

The present invention relates to amniotic fluid specific polypeptide and a method for detecting rupture of the amniotic membranes. In particular the invention provides a marker for prolonged rupture of the membranes (PROM), which marker consists essentially of polypeptides of approximately 75 kDa, 20 kDa and 50 kDa as determined by 4-15% gradient SDS-PAGE under reducing conditions.

18 Claims, 7 Drawing Sheets

MARKER FOR PROLONGED RUPTURE OF MEMBRANES

FIELD OF THE INVENTION

The present invention relates to amniotic fluid specific polypeptide and a method for detecting rupture of the amniotic membranes. In particular, the present invention relates to a marker for prolonged rupture of the membranes (PROM), which marker consists essentially of polypeptides of approximately 75 kDa, 20 kDa and 50 kDa as determined by 4-15% gradient SDS-PAGE under reducing conditions.

BACKGROUND OF THE INVENTION

Diagnosis of rupture of the amniotic membranes prior to the onset of uterine contractions remains one of the significant clinical problems in modern obstetrics because there is not a reliable clinical method for the detection of amniotic fluid in the vagina (Gregg, (1992), *Obstet. Gynecol. Clin. North Am.*, 19: p 241; Malee, (1992), *Obstet. Gynecol. Clin. North Am.*, 19: p 309; Zlatnic, (1992), *Obstet. Gynecol. Clin. North Am.*, 19: p 353; Davidson, (1991), *Clin. Obstet. Gynecol.*, 34: p 715).

Pre-labour rupture of the fetal membranes occurs in 6.6 to 13.9% out of all patients and is followed by spontaneous labour within 48 hours in 70 to 90% of cases (Sacks et al., (1967), *Am. J. Obstet. Gynecol.* 83: p 930; Eastman et al., (1961), *Williams Obstetrics*, Appleton-Century-Crofts, New York pp. 432; Lebherz et al., (1963), *Am. J. Obstet. Gynecol.*, 87: p 218). Pre-labour rupture of the amniotic membranes is directly or indirectly responsible for 4.5-14% of premature births and for significant mortality and morbidity associated with preterm delivery (Friedman et al., (1969), *Am. J. Obstet. Hynecol.* 104: p 544); Gibbs et al., (1982), *Obstet. Gynecol.* 60: p 671). The risks of fetal and maternal infection that accompany expectant management has to be balanced against the improvement in neonatal outcome that arises with greater maturity of the fetal organ systems. The reported latent period between rupture of the membranes and the birth varies between 12 hours and 77 days. Approximately 41% of these women will deliver within a week (Dowd et al., (1992), *Aust. NZ. J. Obstet. Gynaecol.* 32: p 120). Conservative management that leads to prolonging the pregnancy provides the fetus with the greatest potential for survival as outcome reflects gestational age at birth. However, pulmonary hypoplasia and infection may occur with prolonged leakage leading to oligohydramnios (Levine et al., (1991), *Nurse Res.*, 40: p 36; Mercer supra; Morales et al., (1993), *Am. J. Obstet. Gynecol.* 168: p 503; Harstad et al., (1993), *Am. J. Perinatol.* 10: p 8).

In separate studies of 109 and 111 pregnancies respectively studied neonatal outcomes following premature, pre-labour or prolonged rupture of the membranes (PROM) at or before 34 weeks showed an overall mortality of 16.8-26.6% and morbidity of 68.8% (Airede, (1992), *Ann. Trop. Paediatr.* 12: p 283; Dale et al., (1989), *Eur. J. Obstet. Gynecol. Reprod. Biol.* 30: p 257). The occurrence of PROM at or less than 34 weeks was associated with the following complications:

prematurity
chorioamnionitis
neonatal sepsis
cardiorespiratory depression at birth
respiratory distress syndrome (RDS), and
intraventricular haemorrhage
(See, for example, Gjerdingen (1992), *J. Am. Board Fam. Pract.* 5: p 601; Johnson et al., (1981), *Obstet. Gynecol.* 57: p 547; Pasweg et al., (1992), *Gynakol. Geburtshilfliche Rundsch.* 32: p 222; Kilbride et al., (1989), *Clin. Perinatol.* 16: p 863).

Some factors that are frequently associated with the risk of infection are gestational age, elapsed time between rupture and delivery, and socioeconomic status of the mother. Perinatal mortality rate increases two-fold after a latent period of 24 hours, doubles again within 48 hours, and after 14 days is ten times the expected rate (Overstreet et al., (1966), *Am. J. Obstet. Gynecol.*, 96: p 1037; Major, supra). Similarly, maternal morbidity and mortality in certain populations are considerably increased with an extended latent period between rupture of the membranes and delivery (Neuhaus, 1956 and Eastman, supra).

The establishment of a simple and accurate method for diagnosis of premature rupture of the membranes has been a highly desirable outcome for sometime. In some cases the diagnosis of PROM is obvious from the sudden release of clear amniotic fluid from the vagina and its continued presence thereafter. In other cases PROM is less obvious, and it can be difficult to differentiate between the leakages of amniotic fluid from the presence of urine or endocervical mucus in the vagina.

There are currently a number of non-invasive procedures for diagnosing PROM. These include:

Identification of fetal squamous cells or hairs (Phillip et al., (1929), *Zentrabl. Gynakol.* 26: p 1618);
Microscopy for the identification of fetal fat globules within or outside fetal cells following staining (Friedman et al., (1969), *Am. J. Obstet. Gynecol.* 104: p 544;
Estimation of vaginal fluid pH (Nitrazine paper test) (Minkoff et al., (1987), *Am. J. Obstet. Gynecol.* 150: p 965; International Patent Application No. WO02/054949; U.S. Pat. No. 4,357,945);
Amniotic fluid crystallization patterns following desiccation (Gorodeski et al., (1982), *J. Perinat. Med.* 10: p 286; Reece et al., (1984), *Obstet. Gynecol.* 64: p 248; Brookes et al., (1986), *Aust. NZ. J. obstet. Gynecol.* 26: p 160);
Amniotic fluid heating (Dalkalitsis et al., (1989), *Z. Geburtshuilfe. Perinatol.* 193: p 183);
Measurement of the activity of diamine oxidase in vaginal fluid (Gahl et al., (1982), *Obstet. Gynaecol.* 60: p 297);
Prolactin in vaginal fluid (Huber et al., (1983), *Br. J. Obstet. Gynaecol.* 90: p 1183);
Alpha feto-protein in vaginal fluid (Garite, (1990), *Am. J. Obstet. Gynecol.* 151: p 1001);
Insulin-like growth factor binding protein-1 in vaginal fluid (Rutanen et al., (1993), *Clin. Chim. Acta.* 214: p 73; Woltmann et al., (1995), *Z. Geburtshilfe. Neonat.* 199: p 243; Darj et al., (1998), *Acta. Obstet. Gynecol. Scand.* 77: p 295; Ragosch et al., (1996), *Geburtshilfe Fravenheilkd.* 56: p 291; U.S. Pat. Nos. 5,554,504); 5,597,700);
Human placental lactogen in vaginal fluid Huber et al., (1983), *Br. J. Obstet. Gynaecol.* 90: p 1183;
Colorimetric detection (bromothymol blue) (GB Patent No. 2,353,357);
Measurement of inhibin B (International Patent Application No. WO98/59245);
Fetal fibronectin in vaginal fluid (Rutanen supra; Ragosch supra; Trovo et al., (1998), *Minerva Ginecol.* 50: p 519); and
PROM-Protein, (International Patent Application No. WO94/21687).

However, while all of these procedures provide some indication that PROM has taken place they are not completely accurate. In the most part, previously investigated markers for diagnosing PROM provided false positive results owing to the presence of interfering substances. Such substances for the most part are common and which occur in the vagina, examples of these are urine, meconium, pregnancy serum and blood. In many instances, the presence of blood is responsible for a false positive as the markers tested are also found at varying levels in maternal blood (Huber J et al., 1981, *Br J Obstet Gynaecol,* 57:547; Phocas et al., 1989, *Eur J Obstet Gynecol Reprod Biol.,* 31:133; Broe et al., 1992, *Clin Chem.,* 38:784; Hellemans et al., 1992, *Eur J Obstet Gynecol Reprod Biol.,* 43:173.

The inventor has now developed a simple method of determining whether or not amniotic fluid is released prematurely, which is non-invasive and accurate.

SUMMARY OF THE INVENTION

The present inventor has identified novel polypeptides which are specific to amniotic fluid and are absent or present in very low levels in maternal serum.

The present inventor has also found that the predominate polypeptide was 75 (+4) kDa when sized by sodium dodecyl sulfate polyacrylamide electrophoresis (SDS-PAGE), while the two minor polypeptides were of molecular weight 20 (+5) kDa and 50 (+5) kDa. These polypeptides were not present in sera taken from pregnant women, they were only located in amniotic fluid taken from these women.

The inventor further confirmed that these polypeptides, in particularly the 75 (+4) kDa polypeptide, was useful as markers for PROM. Results from further research have also shown that these polypeptides are markers for PROM.

Accordingly, in a first aspect the present invention provides a marker for prolonged rupture of the membranes (PROM), which marker consists essentially of polypeptides of approximately 75 kDa, 20 kDa and 50 kDa as determined by 4-15% gradient SDS-PAGE under reducing conditions.

Preferably, the marker is isolated from the amniotic fluid of a pregnant human subject. More preferably, the marker consists essentially of a 75 (+4) KDa polypeptide isolated from amniotic fluid.

In a second aspect, the present invention provides a method of detection of a marker for prolonged rupture of the membranes (PROM) from a maternal sample taken from a pregnant human, which method comprises determining in the maternal sample the presence of polypeptides of approximately 75 kDa, 20 kDa and 50 kDa as determined by 4-15% gradient SDS-PAGE under reducing conditions.

In one embodiment, the polypeptides consist essentially of proteins of the approximate molecular weights 75 kDa, 20 kDa and 50 kDa. Preferably, the polypeptide is 75 (+4) kDa.

Maternal samples useful for practicing the methods of the invention include, but are not limited to, a fluid present in the vagina of a pregnant human or a tissue which is either contiguous to the fluid or otherwise interactive with the fluid in such a way that its biochemical constituency is fairly representative of the state of the fluid at any given time during gestation. Examples of fluids include cervicovaginal fluids, e.g., cervical fluid or vaginal fluid, urine, plasma and serum. Cervical fluid is preferred.

Fluid samples, which are preferred, may be conveniently obtained from pregnant women by any conventional method known to those skilled in the art. For example, the maternal sample may be obtained directly from the subject by a swab or other suitable collection device, or by a washing using a suitable buffer.

In a third aspect the present invention provides a method of diagnosing prolonged rupture of the membranes (PROM) in a pregnant human, which method comprises determining in the maternal sample the presence of polypeptides of approximately 75 kDa, 20 kDa and 50 kDa as determined by 4-15% gradient SDS-PAGE under reducing conditions.

In a fourth aspect the present invention provides a diagnostic kit for the detection of prolonged rupture of the membranes (PROM) in a pregnant human comprising as a positive control polypeptides of approximately 75 kDa, 20 kDa and 50 kDa as determined by 4-15% gradient SDS-PAGE under reducing conditions which polypeptides have been isolated from amniotic fluid taken from a pregnant human.

In a fifth aspect the present invention provides one or more antibodies capable of selectively binding to polypeptides of approximately 75 kDa, 20 kDa and 50 kDa as determined by 4-15% gradient SDS-PAGE under reducing conditions which polypeptides have been isolated from amniotic fluid taken from a pregnant human.

In a sixth aspect the present invention provides one or more antibodies that are specific to polypeptides of approximately 75 kDa, 20 kDa and 50 kDa as determined by 4-15% gradient SDS-PAGE under reducing conditions which polypeptides have been isolated from amniotic fluid taken from a pregnant human.

In a seventh aspect the present invention provides a method for the detection of prolonged rupture of the membranes (PROM) in a mammal, comprising the steps of: 1) obtaining a maternal sample from a pregnant mammal; 2) contacting the sample with one or more antibodies to polypeptide markers of approximately 75 kDa, 20 kDa and 50 kDa found in amniotic fluid, to allow formation of complexes of the antibodies and the polypeptide markers; and 3) detecting the antibody-marker complexes.

In an eighth aspect the present invention provides a kit for use in detecting the presence of polypeptide markers of approximately 75 kDa, 20 kDa and 50 kDa in a maternal sample taken from a pregnant human subject, comprising: 1) a means for acquiring a quantity of a maternal sample; 2) a media having affixed thereto one or more capture antibodies capable of complexing with polypeptide markers of molecular weight 75 kDa, 20 kDa and 50 kDa as determined by 4-15% gradient SDS-PAGE, which markers are found in amniotic fluid and are predictive of prolonged rupture of the membranes (PROM), which markers; and 3) an assay for the detection of complexes of the polypeptide markers and the capture antibodies.

In an ninth aspect the present invention provides a competitive enzyme linked immunosorbent assay (ELISA) kit for determining the prolonged rupture of the membranes (PROM) status of a pregnant human subject, comprising antibodies specific to the 75 kDa, 20 kDa and 50 kDa polypeptide markers for prolonged rupture of the membranes (PROM), which markers are present in amniotic fluid.

DETAILED DESCRIPTION OF THE INVENTION

Figure 1:
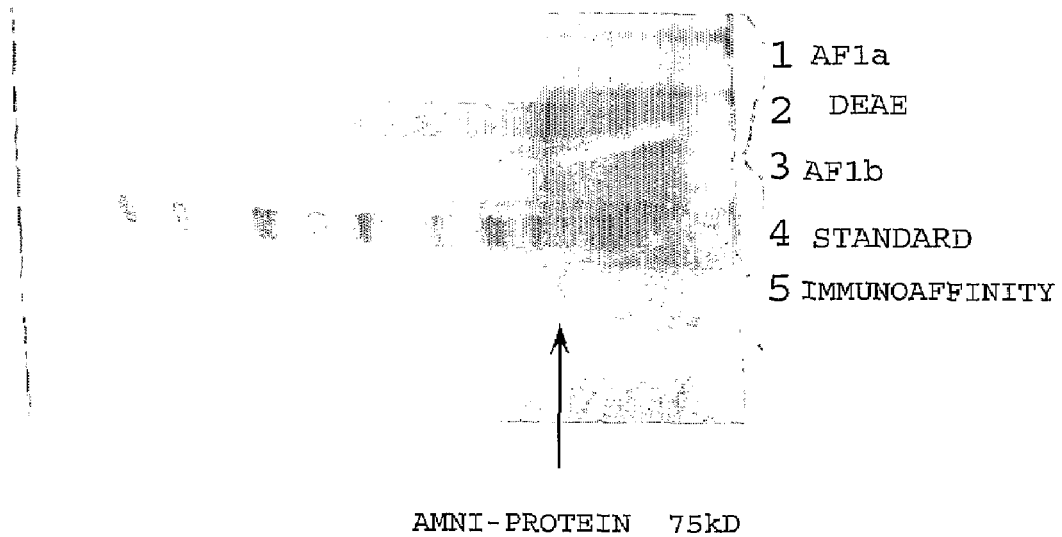
FIG. 1. Western blot and protein staining of proteins onto nitrocellulose membrane following electrophoresis of samples in a 4-20% gradient gel under denaturing conditions. Blotted proteins were treated with MAb 12D2/C6 prior to addition of an ALP conjugate and visualised with NCIB substrate. Lane 1 & 3 shows fraction AF1 from 2 separate runs as applied to the size exclusion column and monitored by 1-site EIA (AF1a and AF1b); Lane 2 shows AF1 post-DEAE treatment; Lane 4 shows benchmark pre-stained standards; and Lane 5 shows immunoaffinity purified PROM-specific protein of the present invention.

Before describing the present invention in detail, it is to be understood that this invention is not limited to particularly exemplified cell culture techniques, serum, media or methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention will employ, unless otherwise indicated, conventional techniques of cell biology, cell culture, molecular biology, recombinant DNA, and immunology, which are within the skill of the art. Such techniques are described in the literature. See, for example, Molecular Cloning: A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Methods In Enzymology (Academic Press, Inc., N.Y.); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986). It must be noted that as used herein and in the appended claims, the singular forms "a," "an," and "the" include plural reference unless the context clearly dictates otherwise. Thus, for example, a reference to "a diagnostic sample" includes a plurality of such samples, and a reference to "an antibody" is a reference to one or more antibodies, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In its broadest aspect the present invention provides a marker for prolonged rupture of the membranes (PROM). The term "marker" or "markers" as used herein refers to the marker for prolonged rupture of the membranes (which will also be referred to as PROM marker). The PROM marker can be any marker, such as any one of the polypeptides described herein, which are present in amniotic fluid of a pregnant human or a combination thereof. An effective PROM marker is typically one of or combination of the 75 (+4) kDa, 20 (+5) kDa and/or 50 (+5) kDa polypeptides described herein; however, the marker may also be mRNA encoding for these polypeptides or genomic DNA molecules encoding the same. As discussed elsewhere, the 75 (+4) kDa, 20 (+5) kDa and/or 50 (+5) kDa polypeptides can be isolated from amniotic fluid, wherein the polypeptides can be sized by 4-15% gradient SDS-PAGE under reducing conditions.

In one embodiment, the PROM marker consists essentially of a 75 (+4) kDa polypeptide as determined by 4-15% gradient SDS-PAGE under reducing conditions. In another embodiment, the PROM marker comprises a composition consisting essentially of polypeptides of molecular weights 75 (+4) kDa, 20 (+5) kDa and/or 50 (+5) kDa as determined by 4-15% gradient SDS-PAGE under reducing conditions, wherein said polypeptides are isolated from amniotic fluid.

The present inventor has identified that the PROM markers of the present invention and in particular the 75 KDa polypeptide is specific to amniotic fluid and is absent or present in very low levels in maternal serum. This led to the discovery that the PROM markers could be used to assess whether or not PROM was taking place. Essentially, the inventor predicated that if one or more of the PROM markers of the present invention were present in a maternal sample, then amniotic fluid is very likely to be present, suggesting that PROM has taken place.

The term "maternal sample" as used herein refers to any sample taken from a pregnant, female mammal. Preferably, the mammal is a pregnant human.

Maternal samples useful for practicing the methods of the invention include, but are not limited to, a fluid present in the vagina of a pregnant mammal or a tissue which is either contiguous to the fluid or otherwise interactive with the fluid in such a way that its biochemical constituency is fairly representative of the state of the fluid at any given time during gestation. Examples of fluids include cervicovaginal fluids, e.g., cervical fluid or vaginal fluid, urine, plasma and serum. In one embodiment, the maternal sample is cervical fluid. Fluid samples, which are preferred, may be conveniently obtained from pregnant women by any conventional method known to those skilled in the art. For example, the maternal sample may be obtained directly from the subject by a swab or other suitable collection device, or by a washing using a suitable buffer.

Once taken, the maternal sample may be analysed directly, or may be treated prior to testing by, for example, filtering, concentrating or pH adjusting. In one embodiment, the maternal sample is treated with one or more mucolytic agents to overcome the presence of cervical mucus. A number of mucolytic agents can be used including N-acetylcysteine derivatives, dithiothreitol, gelsolin, hypertonic saline, mucinase enzymes, or proteolytic enzymes. In one preferred embodiment, the mucolytic agent is N-acetylcysteine (NACC) at a concentration between 0.08 and 8% in phosphate buffered saline (PBS) adjusted to pH7.0 with 1 M NaOH and 100 mM sodium tetraborate pH8.4. The detection or quantitation of the prolonged rupture of the membranes marker in the maternal sample is then undertaken.

The "detection or quantitation" of a marker of the present invention can be accomplished by any appropriate method including an immunological assay or a molecular-biological assay. When the marker is PROM polypeptide, the above method includes, for example, an immunological assay such as Enzyme Linked Immuno Sorbent Assay (ELISA), Radio Immuno Assay (RIA), fluorescence antibody technique, SDS-PAGE, Western blot or an immune structure dyeing method.

When the PROM marker is a polynucleotide such as, mRNA, the assay includes a molecular-biological assay, for example, Northern blot, Dot blot or polymerase chain reaction (PCR). mRNA can be detected or quantitated by using a PROM marker polynucleotide or fragment thereof as a probe or primer.

In one embodiment, the "detection or quantitation" is by SDS-PAGE using a 4 to 20% polyacrylamide gel in accordance with Laemmli, Nature, 227: 680-685, 1970. Preferably, the gradient gels are: 4-15% polyacrylamide gradient gels with a 4% stacking gel. Once the SDS-PAGE gels have run for the required time they are stained with a commercial dye such as 0.25% Coomassie Brilliant Blue R250 (CBB) dissolved in 50% methanol-10% acetic acid to reveal the polypeptide bands. The presence or absence of the 75 (+4) kDa, 20 (+5) kDa and/or 50 (+5) kDa polypeptides of the present invention can be determined readily by assessing their sizes against a known standard.

Alternatively, in another preferred embodiment, the "detection or quantitation" of the 75 (+4) kDa, 20 (+5) kDa and/or 50 (+5) kDa polypeptides of the present invention is by Western Blot or ELISA. As appreciated by those skilled in the art, both of these techniques require the use of antibodies directed to the 75 (+4) kDa, 20 (+5) kDa and/or 50 (+5) kDa PROM polypeptides of the present invention. By using an antibody against the PROM polypeptides or fragments thereof, PROM can be detected or quantitated.

Both monoclonal and polyclonal antibodies that bind to the 75 (+4) kDa, 20 (+5) kDa and/or 50 (+5) kDa polypeptide markers of the present invention are useful in the methods and kits of the present invention. The antibodies can be prepared by methods known in the art.

To prepare polyclonal antibody, typically full length polypeptides or a parts thereof or polypeptides which include a part of the 75 (+4) kDa, 20 (+5) kDa and/or 50 (+5) kDa polypeptides are given as an antigen to a mammal. The polypeptides themself and a carrier, for example, a carrier combined with cattle serum albumin (BSA), keyhole limpet hemocyanin (KLH) or bovine thyroglobulin (BTG) can be used as an antigen. To enhance immune reactions with antigens, for example, complete Freund adjuvants (CFA) and incomplete Freund adjuvants (IFA) can be given. A mouse, a rat, a rabbit, a goat or a hamster can be used as a mammal to immunize. A well known method for producing polyclonal antibodies can be found in Lane et al. (Antibodies: A Laboratory Manual, Second Edition (1989) (Cold Spring Harbor Laboratory Press)). Briefly, after the first immunization, a mammal is immunized by an appropriate antigen 3 to 10 times at 1 to 2-week intervals.

A preferable dosage of the antigens is 50 to 100 µg at one time per animal. When peptides are used, peptides covalently bonded to appropriate carriers are preferably used as antigens. Peptides as antigens can be synthesized by a method of genetic engineering or a peptide synthesizer. Three to seven days after immunization, blood is collected and the responsiveness of the serum against the antigens can be measured by ELISA, see for example, Igaku-Shoin Ltd. (1976), *Antibodies: A Laboratory Manual*, Second Edition (1989) (Cold Spring Harbor Laboratory Press). Blood is then periodically collected from the immunized mammal until the immunized mammal shows a sufficient antibody titre, and then polyclonal antibodies can be prepared from the serum.

Separation and purification of polyclonal antibodies can be accomplished by chromatography such as a centrifugal separation, salting-out with ammonium sulfate, precipitation with caplyric acid (see, for example, Antibodies: A Laboratory Manual, Second Edition (1989) (Cold Spring Harbor Laboratory Press), DEAE-sepharose column, anion exchange column, protein A column or G-column or a gel filter column.

Once the mammal used to produce polyclonal antibodies has reached an appropriate titre it can also be used to prepare monoclonal antibodies against the 75 (+4) kDa, 20 (+5) kDa and/or 50 (+5) kDa polypeptides of the present invention. In this procedure spleens or lymph nodes are extracted from the mammal and used to produce hybridoma by fusing an antibody-producing cell from the spleen or lymph node with a myeloma cell. As for the myeloma cell, cells established from a mouse or a rat can be used. Cell fusion can be done according to already known methods, for example, see Kohler and Milstein (1975) (Nature, 256, 495-497).

The 75 (+4) kDa, 20 (+5) kDa and/or 50 (+5) kDa polypeptides, parts thereof or polypeptides including these polypeptides or parts thereof are injected into a rat. Three to seven days after the rat has shown a sufficient antibody titre, the rat is immunized with the antigen for the last time, and its spleen is extracted as antibody producing cells. The spleen is cut into pieces in MEM medium (Nissui Pharmaceutical Co. Ltd.) and the dissociated cells are precipitated by centrifugation at 1,200 rpm for 5 minutes. Splenocytes are separated by treating the precipitant with Tris-ammonium chloride buffer (pH 7.65) for 1 to 2 minutes to remove red blood cells. The splenocytes are washed with MEM medium 3 times and are used as antibody producing cells.

In order to establish a cell line myeloma cells are isolated from a mouse or rat. Appropriate myeloma cells can be isolated from the following strains: BALB/c (8-azaguanine resistance mouse), P3-X63Ag8-U1 (described as P3-U1) (Current Topics Microbiological Immunology, 81, 1 (1978), *SP*2/0-Ag14 (described as SP-2) (Nature, 276, 269 (1978).), P3-X63-Ag8653 (described as 653) (Journal of Immunology, 123, 1548 (1979).) or P3-X63-Ag8 (described as X63) (Nature, 256, 495 (1975).). These cell strains are subcultured in a 8-azaguanine medium (a normal medium including 15 µg/ml 8-azaguanine (RPMI1640 medium including 1.5 mM glutamine, $5 \times 10^{-5}$ M 2-mercaptoethanol, 10 µg/ml gentamysin and 10% FCS made by CSL)) and cultured in a normal medium for 3 to 4 days before cell fusion. $2 \times 10^7$ or more cells are prepared for cell fusion.

Hybridoma cells and myeloma cells are then mixed and washed with MEM medium or PBS (per 1 L; 1.83 g sodium phosphate dibasic, 0.21 g monobasic potassium phosphate, 7.65 g NaCl, pH7.2) and mixed as the number of antibody producing cells is 5 to 10 times larger than that of the myeloma cells. After a centrifugal separation at 1,200 rpm for 5 minutes, a precipitant is obtained. The precipitated cells are resuspended in 0.2 to 1 ml of polyethylene glycol solution (2 g polyethylene glycol-1000 (PEG-1000), 2 ml MEM medium, 0.7 ml dimethyl sulfoxide (DMSO)) per $10^8$ antibody producing cells is added to the cells with stirring at 37° C. 1 to 2 ml of MEM medium is then added several times every 1 to 2 minutes. The solution is prepared with MEM medium to 50 ml in total. After a centrifugal separation at 900 rpm for 5 minutes, a precipitant is obtained. 100 ml of HAT medium (normal medium including $10^{-4}$M hypoxanthine, $1.5 \times 10^{-5}$ M thymidine and $4 \times 10^{-7}$M aminopterin) is added to a precipitant and the precipitant is slowly resuspended. The suspension is poured into the 96-well culture plate at 100 µl per well and cultured at 37° C. in the presence of 5% $CO_2$ for 7 to 14 days.

By the method described in Antibodies: A Laboratory Manual, Second Edition (1989) (Cold Spring Harbor Laboratory Press), hybridomas producing antibodies specifically reacting with 26.6 Kd polypeptide are selected.

Methods of detecting the PROM polypeptides or parts thereof using the antibodies described above can involve direct or indirect bonded enzymes, fluorescent substances, radioisotopes or latexes. The assay method, for example, can be ELISA or a chemiluminescence method detecting enzyme activities such as horseradish peroxidase or alkaline phosphatase, FITC method detecting fluorescent tags such as luminol or GFP (Green Fluorescence Protein), RIA method detecting radioisotope tags such as $^{125}$I or a latex agglutination method detecting binding with latex. The assay can also be, for example, Western blot or immune structure dyeing. Furthermore, the 75 (+4) kDa, 20 (+5) kDa and/or 50 (+5) kDa polypeptides or a parts thereof can be quantitated by the assay.

The antibodies used in the immunoassays can be immobilized to a solid phase carrier and the trapped polypeptides can be detected by using secondary antibodies with a reporter group or using reagents. Any substance, to which antibodies can attach and which is widely known to persons of ordinary skill in the art, can be used as a solid phase carrier. The substance includes, for example, a microtitre plate, a membrane such as a nitrocellulose membrane, bead, disk, glass, glass fibre, plastic material such as latex, polystyrene or polyvinyl chloride. Magnetic particles or fibre optical sensors (U.S. Pat. No. 5,359,681) can be used.

In this description, "solid phase" means immobilization by a physical method such as adsorption or a chemical binding by a covalent bond between an antibody and a functional group on a carrier. An antibody and a functional group on a carrier can be bonded directly or through a cross-linking agent. Immobilization by a physical method can be accomplished by appropriately diluted antibodies contacted with a carrier, preferably, a microtitre plate or a membrane in an appropriate buffer for an appropriate time. The contact time varies depending on the temperature, but it is typically between about 1 hour and 1 day. About 10 ng to 1 µg, preferably, about 100 to 200 ng of antibodies is added and immobilized on each well of a microtitre plate made of plastic such as polystyrene or polyvinyl chloride. Immobilization by a chemical method can be accomplished by a reaction of a carrier and functional groups of antibodies, for example, a reaction of a carrier and a two-functional reagent that reacts with both hydroxyl groups and amino groups and a carrier. For example, antibodies can be immobilized to a carrier having an appropriate polymer coat with a covalent bond by using benzoquinone or a condensation between aldehyde groups on a carrier and an amine or an active hydrogen on a combination partner.

A carrier-immobilized antibody is treated to inhibit physical adsorption of other polypeptides by a well-known method for a person having ordinary skill in the art with an appropriate blocking reagent, for example, cattle serum albumin or Tween 20 (Sigma-Aldrich). A carrier-immobilized antibody is reacted with a sample and polypeptides of the present invention and antibodies are combined. A maternal sample can be appropriately diluted with an appropriate diluent, for example, phosphate buffered saline solution (PBS). A reaction time of a maternal sample and antibodies should be enough to detect the presence of polypeptides of the present invention in a maternal sample obtained from an individual suspected as having PROM, preferably, a time to achieve at least 95% of binding level compared to the level at which bound and not-bound polypeptides are equilibrated.

A time to reach equilibrium can be easily decided by measuring the binding level by the time. Substances other than bound polypeptides can be removed by washing a solid carrier with an appropriate buffer, for example, PBS (including 0.1% Tween 20). Labelled secondary antibodies are reacted with a solid carrier. The labels are preferably enzymes such as horseradish peroxidase, ground substances, supplemental elements, inhibitors, pigments, radioisotopes, colouring substances or fluorescent substances.

The binding between antibodies and labels can be accomplished by well-known methods. The secondary antibodies are reacted for a sufficient time to bind to complexes, which include immobilized antibodies and polypeptides of the present invention. An appropriate time can be easily decided by measuring binding level by the time. The non-binding secondary antibodies can be removed by washing a solid carrier with an appropriate buffer, for example, PBS (including 0.1% Tween 20). The method of detection of labels of the secondary antibodies depends upon the kind of labels used. For example, when radioisotopes are used as labels, detection by a scintillation counter or an autoradiography can be used. When pigments, colouring substances or fluorescent substances are used as labels, detection by a spectrophotometer can be used. When enzymes are used as labels, substrates for the enzymes are added and reacted for a fixed time and the products are detected by a spectrophotometer. Labels and secondary antibodies can bind directly or indirectly by an avidin-biotin method. When they bind indirectly, one part of the avidin-biotin is bound to a secondary antibody and another is bound to a label. 75 (+4) kDa, 20 (+5) kDa and/or 50 (+5) kDa polypeptides can be detected by a flow through test or a strip test.

In a flow through test, a maternal sample is added to a nitrocellulose membrane on which antibodies are immobilized, and when a sample passes through the membrane, polypeptides bind to the immobilized antibodies to form immune complexes. When a solution including labelled secondary antibodies passes through the membrane, it binds to the immune complexes. In a strip test, once a maternal sample is added, the maternal sample passes through a region including labelled antibodies, and polypeptides bind to labelled antibodies to form immune complexes.

When a maternal sample passes through a region including a solid phase antibody, polypeptides bind to the immune complexes. The quantity of secondary antibodies detected in the region with immobilized antibodies shows the presence or absence of PROM.

An alternative to the "detection or quantitation" of the polypeptide of the present invention is the "detection or quantitation" of polynucleotides encoding the PROM polypeptides. The polynucleotides encoding the PROM markers of the present invention can be used as markers for PROM. The polynucleotide sequences encoding the 75 (+4) kDa, 20 (+5)

kDa and/or 50 (+5) kDa polypeptides of the present invention can be detected and measured using standard molecular-biologically techniques.

One method of detecting the presence of the polynucleotides encoding the 75 (+4) kDa, 20 (+5) kDa and/or 50 (+5) kDa polypeptides is use of a probe or a primer, which includes nucleotides having the same sequence as the coding sequence of the polypeptides or oligonucleotides having sequences complementary to the sequences of the coding sequences of the polypeptides or derivatives thereof. A derivative thereof includes, for example, a oligonucleotide wherein a phosphodiester bond in the oligonucleotide is transformed into a phosphorothioate bond or a N3'-P5' phosphoamidite bond, a oligonucleotide wherein a ribose and a phosphodiester bond are transformed into a peptide bond, a oligonucleotide wherein a uracil in the oligonucleotide is substituted with a C-5 propionyl uracil or a C-5 thiazole uracil, a oligonucleotide wherein a cytosine in the oligonucleotide is substituted with C-5 propionyl cytosine or cytosine modified with phenoxazine or a oligonucleotide wherein a ribose in DNA is substituted with 2'-O-propyl ribose, 2'-methoxyethoxy ribose or the like. All of the above described polynucleotides are useful, for example, as gene markers, as primers for PCR or as probes for hybridization. The present invention relates to a part or all of the polynucleotides encoding the PROM markers of the present invention.

It is also possible that the coding sequences for the 75 (+4) kDa, 20 (+5) kDa and/or 50 (+5) kDa polypeptides can be isolated, sequenced and/or expressed in vitro. In order to accomplish this a cDNA library, including the polynucleotides encoding the 75 (+4) kDa, 20 (+5) kDa and/or 50 (+5) kDa polypeptides of the present invention, are prepared from human brain, heart, skeletal muscle, spleen, kidney, liver, small intestine, placenta, human normal cells from these tissues or human umbilical vein endothelial cells. A useful method for making cDNA libraries is described in Molecular Cloning: A Laboratory Manual, Second Edition (1989) (Cold Spring Harbor Laboratory Press), Current Protocols in Molecular Biology (1994) (Wiley-Interscience). There are also commercially available kits, for example, SuperScript Plasmid System for cDNA Synthesis and Plasmid Cloning (Invitrogen) or ZAP-cDNA Synthesis Kits (STRATAGENE). Once cDNA including DNA encoding the polypeptides of the present invention are obtained they can be inserted into an appropriate expression vectors. The expression vectors can then be introduced into appropriate hosts and transformants obtained.

The expression vectors are any vectors in which cDNA is inserted and which express in animal cells. Suitable vectors include, for example, pcDNA1.1, pcDNA1.1/Amp, pCDM8, pREP (Invitrogen), pHM6, pHB6 (Roche Diagnostics), pKK223-3, PGEX (Amersham Pharmacia Bioteque), pET-3, pET-11, pBluescriptII SK(+), pBluescriptII SK(−) (STRATAGENE), pUC19, pTrxFus (Invitrogen), pUC118, pSTV28 (TaKaRa), pMAL-c2X (New England BioLabs), pAGE107 (Cytotechnology, 3 (2), 133-140 (1990); JP1991-22979), pAGE103 (The Journal of Biochemistry, 101 (5), 1307-1310 (1987).), pAMo, pAMoA (The Journal of Biological Chemistry, 268 (30), 22782-22787 (1993).), pAMoPRSA (JP1993-336963) or pAS3-3 (JP1990-227075).

Expression vectors, containing the cDNA encoding the 75 (+4) kDa, 20 (+5) kDa and/or 50 (+5) kDa polypeptides, are introduced into optional animal cells by any method known in the art. When the host is animal cell the following, non-limiting methods may be used: electroporation (Cytotechnology, (1990), 3, 133-140, calcium phosphate method or lipofection (PNAS, USA, (1987), 84, 7413). Appropriate animal cells include Namalwa (Burkitt lymphoma, ATCC: CRL-1432), HCT-15 (human large bowel cancer cell, ATCC: CCL-225), COS-1 (African green monkey's nephrocyte, ATCC: CRL-1650), COS-7 (African green monkey's nephrocyte, ATCC: CRL-1651) and CHO-K1 (Chinese hamster ovary cell, ATCC: CCL-61).

Transformants of the present invention are cultured by generally known and commonly used methods. It can be accomplished with a medium appropriate to a transforming host and a liquid medium. Examples of useful medium are, MEM medium (Science, 130, 432 (1959).), D-MEM medium (Virology, 8, 396 (1959).), PRMI 1640 medium (The Journal of the American Medical Association, 199, 519 (1967).), YT medium or BEM medium can be used. When transformants are prepared using animal cells as the host the medium is usually supplemented with fetal calf serum (FCS). The medium can optionally also include a substance promoting transcription activity to enhance transcription activity of a promoter of an expression vector. For example, isopropyl-1-thio-[beta]-D-galactopyranosin (IPTG) can be used. The medium might also include others nutrients such as glucose, amino acid, peptone, vitamin, hormone or serum, preferably, FCS, calcium chloride or magnesium chloride.

Alternative methods of obtaining cDNA encoding the polypeptides of the present invention include the chemical synthesis of polynucleotide sequences or the production of cDNA from extracted mRNA. For example, on the basis of the amino acid sequence of the 75 (+4) kDa, 20 (+5) kDa and/or 50 (+5) kDa polypeptides of the present invention the polynucleotide sequences can be ascertained. Chemical synthesis of DNA can then be accomplished using a DNA synthesizer by the thiophosphite method (Shimazu Corporation) or using a DNA synthesizer model 392 by the phosphoamidite method (Perkin Elmer, Inc.). cDNA can be prepared from mRNA in cells expressing complementary mRNA of the DNA for the 75 (+4) kDa, 20 (+5) kDa and/or 50 (+5) kDa polypeptides as templates.

When cDNA encoding the 75 (+4) kDa, 20 (+5) kDa and/or 50 (+5) kDa polypeptides have been isolated the DNA can be expressed in vitro. For example, polynucleotide coding for the polypeptides can be made to express in host cells by subcloning the DNA fragment or a full length DNA downstream of a promoter in an appropriate expression vector. The expression vector is then transformed into a prokaryotic cell, yeast, an animal cell, a plant cell or an insect cell. Appropriate expression vectors include pBTrp 2, pBTac1, pBTac2 (Roche Diagnostics), BluescriptII SK(+), pBluescriptII SK(−) (STRATAGENE), pSTV28, pUC118, pUC19 (TaKaRa), pKK233-2 (Pharmacia), pSE280, pSupex, pUB110, pTP5, pC194, pTrxFus (Invitrogen), pGEMEX-1 (Promega), pQE-8 (QIAGEN), pGEX (Pharmacia), pETsystem (Novagen), pMAL-c2 (New England BioLabs), pKYP10 (JP1982-110600), pKYP200 (Agricultural Biological Chemistry, 48, 669 (1984).), pLSA1 (Agricultural Biological Chemistry, 53, 277 (1989).), pGEL1 (Proceedings of the National Academy of Sciences USA, 82, 4306 (1985).), pEG400 (Journal of Bacteriology, 172, 2392 (1990).), pTrs30 (FERM BP-5407), pTrs32 (FERM BP-5408), pGHA2 (FERM BP-400), pGKA2 (FERM BP-6798), pPA1 (JP1987-233798) or pTerm2 (JP1990-22979, U.S. Pat. Nos. 4,686, 191, 4,939,094, 5,160,735).

Any promoter which can express in a host cell such as *Escherichia coli* can be used. For example, it is a promoter from *Escherichia coli* or a phage such as trp promoter (Ptrp), lac promoter (Plac), PL promoter, PR promoter or PSE promoter, SPO1 promoter, SPO2 promoter or penP promoter.

Host cells include a prokaryote of *Escherichia* genus, *Serratia* genus, *Bacillus* genus, *Brevibacterium* genus, *Corynebacterium* genus, *Microbacterium* genus or *Pseudomonas* genus. For example, *E. coli* strains XL1-Blue, XL2-Blue, DH1 strain, MC1000, KY3276, W1485, JM109, HB101, No. 49, W3110, NY49, BL21 (DE3), BL21 (DE3) pLysS, HMS174 (DE3) or HMS174 (DE3) pLysS can be used. Yeast cells that can be used as hosts include *S. cerevisiae* species of *Saccharomyces* genus, *S. pombe* species of *Schizosaccharomyces* genus, *K. lactis* species of *Kluyveromyces* genus, *T. pullulans* species of *Trichosporon* genus, *S. alluvius* species of *Schwanniomyces* genus or *P. pastoris* species of *Pichia* genus.

Any method of introducing the expression vector into a host can be used. For example, electroporation, spheroplast method or a lithium acetate method.

When an animal cell is used as a host, the following expression vectors can be used: pcDNA1/Amp, pcDNA1, pCDM8, pREP4 (Invitrogen), pAGE 107 (Cytotechnology, 3, 133 (1990).), pAGE 103 (The Journal of Biochemistry, 101, 1307 (1987).), pAMo, pAMoA (pAMoPRSA) (The Journal of Biological Chemistry, 268, 22782-22787 (1993).) or pAS3-3 (JP1990-22705). Any promoter that can express in a host can be used as a promoter, for example, a promoter of IE (Immediate-early) gene of human cytomegalovirus (hCMV), an early promoter of SV40, Long Terminal Repeat Promoter of Moloney Murine Leulemia Virus, a promoter of retrovirus, HSP promoter, SR [alpha] promoter or a promoter of metallothionein. An enhancer of IE gene of human CMV can be used with a promoter. An animal cell as a host is, for example, HEK293 (a human fetal nephrocyte, ATCC:CRL-1573), Namalwa (Burkitt lymphoma, ATCC:CRL-1432), HeLa (a cell of carcinoma of uterine cervix, ATCC:CCL-2), HBT5637 (a leukemia cell, JP1987-299), BALL-1 (a leukemia cell) or HCT-15 (a large bowel cancer cell) of an established cell from a human, Sp2/0-Ag14 (a mouse myeloma cell, ATCC:CRL-1581) or NSO (a mouse myeloma cell) of an established cell from a mouse, COS-1 (African green monkey nephrocyte (SV40 transformed cell), ATCC:CRL-1650) or COS-7 (African green monkey nephrocyte (SV40 transformed cell), ATCC:CRL-1651) of an established cell from a monkey, CHO-K1 (Chinese hamster ovary cell, ATCC:CCL-61) or BHK-21 (C-13) (Sicilian hamster kidney cell, ATCC:CCL-10) of an established cell from a hamster, PC12 (an adrenal pheochromocytoma, ATCC:CRL-1721) or YB2/0 (a rat myeloma cell, ATCC:CRL-1662) of an established cell from a rat.

Insect cells can also be used as a host. When an insect cell is used as a host, an expression vector is, for example, pVL1392, pVL1393 or pBlueBacIII (Invitrogen) and a virus for infection is, for example, a Vaculovirus which infects insects of Mamestra brassicoe family; *Autographa california* nuclear polyhedrosis virus (AcMNPV) Bac-N-Blue DNA. A transformation method of an insect cell is, for example, a method described in Baculovirus Expression Vector: A Laboratory Manual (1992) (W.H. Freeman and Company), Molecular Cloning: A Laboratory Manual, Second Edition (1989) (Cold Spring Harbor Laboratory Press), Current Protocols in Molecular Biology (1994) (Wiley-InterScience) or Biotechnology, 6, 47 (1988). A transfer vector including a target gene and baculovirus DNA for infection to an insect cell are added into a culture and a virus expressing a target gene produced by recombinant infects an insect cell to be expressed a polypeptide.

An insect cell as a host is, for example, an established cell from *Spodoptera frugiperda* (Mamestra brassicoe) or an established cell from *Trichoplusia ni*. For example, a cell from *S. frugiperda* includes Sf9 (ATCC: CRL-1711, an ovary cell) or Sf21 (an ovary cell) and a cell strain from *T. ni* is, for example, High Five or BTI-TN-5B1-4 (an egg cell, Invitrogen).

Once transformants have been produced and cultured the 75 (+4) kDa, 20 (+5) kDa and/or 50 (+5) kDa polypeptides of the present invention can be isolated and purified. A useful method of isolation/purification of the polypeptides is the method described by Sandler (Methods in Enzymology, 83, 458). When the 75 (+4) kDa, 20 (+5) kDa and/or 50 (+5) kDa polypeptides are produced and accumulated as dissolved polypeptides, the culture solution can be separated from the cells by, for example, centrifugation. If the polypeptides exist in the host cells, the cells are extracted and washed with an appropriate buffer such as STE solution and broken into pieces by ultrasonic waves, French press, Manton Gaulin homogenizer or Dynomill. The resultant material is then separated by centrifugation or filtration.

A method of separation/purification of target proteins from crude material can be accomplished with the combination of all kinds of well-known methods of separation/purification. Well-known methods include, for example, a solvent extraction method, a salting-out method with ammonium sulfate, a dialysis, an sedimentation with an organic solvent, an ultrafiltration method, a gel filtration, all kinds of chromatography such as a diethylaminoethyl (DEAE)-sepharose chromatography, an anion chromatography or an ion exchange chromatography using lysine such as DIAION HPA-75 (Mitsubishi Chemical Corporation), a cation chromatography using lysine such as S-Sepharose FF (Pharmacia), a hydrophobic chromatography or an affinity chromatography such as butylsepharose or all kinds of electrophoresis such as a SDS-polyacrylamide gel electrophoresis or an electro-focussing electrophoresis.

Affinity chromatography can be accomplished by using antibodies against the 75 (+4) kDa, 20 (+5) kDa and/or 50 (+5) kDa polypeptides. When 75 (+4) kDa, 20 (+5) kDa and/or 50 (+5) kDa polypeptides are produced and accumulated as insoluble polypeptides, cells are separated as mentioned above and broken into pieces by an appropriate method. Then a division including the polypeptides are collected. A collected sample is solubilized with a solubilizer like a surfactant such as sodium lauryl sulfate (SDS) or Sodium N-Dodecanoylsalcosinate (salcosiyl). After the solubilized solution is diluted or dialyzed to the concentration that a solubilizer is not or almost not included and the polypeptide is constructed to a normal stereo structure, a purification sample can be obtained by a method of separation/purification as mentioned above.

The present invention also provides a method and kit for assaying the presence of PROM marker present in a maternal sample taken from a mammalian subject suspected of having PROM. Early detection of the PROM can reduce the time for treatment and reduce the risk of developing clinically significant complications.

A simple point-of-care kit that uses principles similar to the widely-used urine pregnancy testing kits, for the rapid detection of the PROM marker will allow the clinician to rapidly diagnose PROM, and to rapidly institute proven and effective therapeutic and preventive measures. The use of the kit can represent the standard of care for all patients who are at risk of developing PROM.

The methods and kits of the present invention can also provide a means for detecting or monitoring PROM including the change in status. Thus, the invention also provides a means for a clinician to monitor the progression of the PROM (worsening, improving, or remaining the same) following treatment. Typically, the clinician would establish a protocol of collecting and analysing a quantity of maternal sample from the patient at selected intervals. Typically the sample is obtained intermittently during a prescribed period. The period of time between intermittent sampling may be dictated by the condition of the subject, and can range from a sample each 24 hours to a sample taken continuously, more typically from each 4 hours to each 30 minutes.

Using the methods and techniques described herein, both a qualitative level of the 75 (+4) kDa, 20 (+5) kDa and/or 50 (+5) kDa polypeptide markers present in the maternal sample can be analysed and estimated, and a quantitative level of the polypeptide markers present in the sample can be analysed and measured. The clinician would select the qualitative method, the quantitative method, or both, depending upon the status of the patient. Typically, the quantity of sample to be collected is less than 1 millilitre, and more typically less than 10 µl. A typical sample can range from about 1 µl to about 1 ml. Once an indication of PROM has been detected, and intervention and treatment of the condition has commenced, the clinician can employ the method and kit of the invention to monitor the progress of the treatment or intervention. Typically, one or more subsequent post-treatment maternal samples will be taken and analysed for the presence of the PROM markers as the treatment of the PROM continues. The treatment is continued until the presence of the 75 (+4) kDa, 20 (+5) kDa and/or 50 (+5) kDa polypeptide markers in subsequent post-treatment maternal samples is not detected. As the treatment and intervention ameliorate the condition, the expression of polypeptide markers, and its presence in the sample, will be correspondingly reduced. The degree of amelioration will be expressed by a correspondingly reduced level of polypeptide markers detected in a sample.

A kit for use in the method typically comprises a media having affixed thereto the capture antibodies, whereby the maternal sample is contacted with the media to expose the capture antibodies to the 26.6 Kd polypeptide markers contained in the sample. The kit includes an acquiring means that can comprise an implement, such as a spatula or a simple stick, having a surface comprising the media. The acquiring means can also comprise a container for accepting the maternal sample, where the container has a serum-contacting surface that comprises the media. In another typical embodiment, the assay for detecting the complex of the polypeptide markers and the antibodies can comprise an ELISA, and can be used to quantitate the amount of polypeptide markers in a maternal sample. In an alternative embodiment, the acquiring means can comprise an implement comprising a cassette containing the media.

A method and kit of the present invention for detecting the polypeptide markers can be made by adapting the methods and kits known in the art for the rapid detection of other proteins and ligands in a biological sample. Examples of methods and kits that can be adapted to the present invention are described in U.S. Pat. No. 5,656,503, issued to May et al. on Aug. 12, 1997, U.S. Pat. No. 6,500,627, issued to O'Conner et al. on Dec. 31, 2002, U.S. Pat. No. 4,870,007, issued to Smith-Lewis on Sep. 26, 1989, U.S. Pat. No. 5,273,743, issued to Ahlem et al. on Dec. 28, 1993, and U.S. Pat. No. 4,632,901, issued to Valkers et al. on Dec. 30, 1986, all such references being hereby incorporated by reference.

A rapid one-step method of detecting the polypeptide markers of the present invention can reduce the time for detecting the development of PROM. A typical method can comprise the steps of: obtaining a maternal sample from a human suspected of PROM; mixing a portion of the sample with one or more detecting antibodies which specifically bind to one or more of the 75 (+4) kDa, 20 (+5) kDa and/or 50 (+5) kDa polypeptide markers, so as to initiate the binding of the detecting antibodies to the polypeptide markers in the sample; contacting the mixture of sample and detecting antibodies with immobilized capture antibodies which specifically bind to the polypeptide markers, which capture antibodies do not cross-react with the detecting antibodies, so as to bind the detecting antibodies to the polypeptide markers, and the 75 (+4) kDa, 20 (+5) kDa and/or 50 (+5) kDa polypeptide markers to the capture antibodies, to form a detectable complex; removing unbound detecting antibody and any unbound sample from the complex; and detecting the detecting antibodies of the complex. The detectable antibodies can be labelled with detectable markers, such as radioactive labels, enzymes, biological dyes, magnetic beads, or biotin, as is well known in the art.

The invention will now be further described by reference only to the following non-limiting examples. It should be understood, however, that the examples following are illustrative, and should not be taken in any way as a restriction on the generality of the invention described herein.

EXAMPLE 1

Identification and Isolation of PROM Markers

In the first stage, amniotic fluid specimens were collected (20-975 mL) from women undergoing a caesarean section. All samples were filtered through glass wool prior to being distributed in 2 mL aliquots into sterile 5 mL centrifuge tubes. One tube from each sample was subsequently used in the preparation of various protein fractions (pools) for use in the immunisation schedule and subsequent clinical evaluation.

Twenty random amniotic fluids of 2 mL were pooled and used in the purification procedure as follows. The entire pool was pretreated with Affi-Gel Blue Gel (AGB [Biorad]) to remove as much of the endogenous albumin as possible. The AGB was prepared by washing with PBS in a 50 mL conical bottom culture tube and centrifuged at 2000 rpm for 10 min. The supernatant was removed and the same volume of fresh buffer was added to the gel, mixed by vortexing, and again centrifuged as above. This procedure was repeated 5 times. AGB was added to the antigen pool in a 1:1 [v/v] ratio and mixed end-over-end for 4 hours. The solution was centrifuged at 2000 rpm for 20 min and the supernatant collected into a fresh 50 mL sterile culture tube. The AGB treated supernatant was then subjected to immunochromatography as described in International patent number WO03/018634. The column employed for this purpose comprised antibodies raised against sera from normal pregnant patients.

Upon removal of the unbound fraction, the amniotic fluid specific proteins were eluted and the pH of each fraction adjusted using 10M Tris within the pH range of 7-7.5, as monitored by pH paper. Those fractions containing potential amniotic fluid specific proteins as determined by SDS-PAGE were pooled and subjected to molecular weight (MW) separation using centrifugal microconcentrators (Filtron, Amicon) with two distinct MW cutoffs. Microconcentrator devices with molecular weight cutoff levels of 300 kDa and 100 kDa were rinsed with 70% ethanol and washed with PBS by centrifugation at 2500 rpm for 10 min. 3.5 mL of the antigen pool was added to the 300 kD cut-off microconcentrator and centrifuged for 90 min at 2500 rpm. The procedure was repeated until one-half of the filtrate, ~1.7-1.8 mL, had passed through into the filtrate receiver. PBS was added to the sample reservoir containing the original pool, mixed, and centrifuged again for 90 min at 2500 rpm. The microconcentrator was again centrifuged for 45 min at 2500 rpm and the supernatant containing the protein fraction with a MW of >300 kDa was transferred to a sterile 15 mL conical-bottomed tube and labeled "AF1".

The filtrate from the first centrifugation stage was then transferred to the second microconcentrator with a 100 kDa cut-off membrane. The microconcentrator was centrifuged for 90 min at 2500 rpm, PBS was added to the sample reservoir and made up to the starting volume of 3.5 mL. The microconcentrator was again centrifuged for 120 min at 2500 rpm. Both the supernatant ("AF2") and filtrate ("AF3") were collected following centrifugation with a 100 kDa membrane into sterile 12 mL conical-bottomed tubes.

Protein estimations are performed on all three collected fractions (i.e. AF1, AF2 & AF3). 150-200 µg of each fraction was mixed with adjuvant for the immunisation schedule. The remainder of the pool was stored at −20° C. in aliquots containing sufficient antigen (i.e. 150-200 µg) for subsequent booster injections.

Amniotic fluid fraction AF1 was further purified using an 12D2/C6 immunoaffinity column and showed a prominent band on a 4-15% SDS-PAGE of sub-unit molecular weight 75 (+4) kDa and two minor bands of molecular weight 20 (+5) kDa and 50 (+5) kDa, which were not seen in maternal sera following similar processing. These bands were present in the pooled and individual amniotic fluid samples, but were not seen in any maternal sera.

EXAMPLE 2

Monoclonal Antibody Production

For primary immunisations of six BALB/c mice, 0.15-0.2 mg of fractions AF1, AF2 and AF3 from Example 1 were emulsified in MPL (1:10 v/v [SIGMA]) and injected subcutaneously into each mouse. Booster immunisations using 0.15-0.2 mg of the respective amniotic fluid fraction prepared with MPL (1:10 v/v [SIGMA]) were given by the same routes. The initial boost was given at three weeks post-immunisation with subsequent boosts prescribed at 7-8 day intervals for 6 weeks. Antibody levels were monitored by collecting eye bleeds 4 weeks post primary immunisation and then weekly until 10 weeks and testing the sera by an indirect one-site enzyme immunoassay.

In the indirect one-site enzyme immunoassay procedure, 100 µL of each amniotic fluid fraction (0.2 mg/mL) in Tris-HCl buffer pH 7.2, two different amniotic fluid (positive controls) and maternal serum (negative controls) AGB pretreated pools were added to each well of 96-well microtitre plates [NUNC Immunoplate: maxisorp] and incubated at room temperature (approx. 25° C.) for 1 hr. Plates were washed 3 times with PBS (low salt (LS))/Tween (16 g/L NaCl [BDH]; 1.15 g/L $Na_2HPO_4.2H_2O$ [BDH]; 0.2 g/L $KH_2PO_4$ [BDH]; 0.2 g/L KCl [BDH] containing 0.2% (v/v) Tween-20 [SIGMA]) and blocked with 200 µL/well PBS(LS) containing 0.5% ovalbumin for 2 hr at room temperature. Plates were washed 3 times with PBS(LS)/Tween, and 100 µL of mouse sera (at different dilutions in PBS (LS)) was then added to each well; blanks were similarly prepared but using 100 µL/well of sera at the same dilution collected from non-immunized BALB/c mice. After incubation at room temperature for 1 hr, plates were washed 3 times with wash buffer and 50 µL/well of peroxidase conjugated goat anti-mouse IgG [Dako] diluted 1:1,000 in PBS(LS)/Tween was added and incubated for a further 1 h at room temperature. Following a further 4 washes, 100 µL/well of ABTS substrate solution (5 mM citric acid [BDH]; 5 mM tri-sodium citrate [BDH]; 0.4 mM azinobis [3-ethylbenzthiazoline sulfonic acid] diammonium salt [SIGMA] activated with 0.003% (v/v) hydrogen peroxide) was added and the reaction allowed to proceed for 30 min. The reaction was stopped with 50 µL/well of 3.9% oxalic acid [SIGMA] and the absorbance was measured in a plate reader (Molecular Devices) at 405 nm.

One mouse was chosen for further treatment and given a final subcutaneous boost of the respective amniotic fluid fraction. Four days later, the mouse was sacrificed by $CO_2$ asphyxiation and the spleen was removed under sterile conditions and placed in a 60 mm Petri dish in RPMI-1640 culture medium. The spleen was perfused with medium by injecting it with a 26-gauge needle at 5 sites, thereby forcing medium into the spleen to release the cells. The cells were transferred to a sterile centrifuge tube, centrifuged (250×g for 10 min) and the supernatant removed. The cells were resuspended in 10 mL culture medium and counted on the Coulter Counter [Coulter]. $1 \times 10^7$ NS1 cells grown in RPMI-1640/10% FCS were similarly centrifuged and resuspended in 10 mL RPMI-1640 and counted. Splenic lymphocytes were fused with NS1 myeloma cells at a ratio of 8:1 using 50% PEG 1500/4000 in RPMI-1640. Hybrids were grown in a selection medium containing HAT (10 mM hypoxanthine; 0.04 mM aminopterin; 1.6 mM thymidine) [GIBCO] $2 \times 10^5$ feeder cells/mL, 20% FCS [TRACE], 100 U/mL penicillin, 50 U/mL streptomycin and 50 U/mL gentamycin in RPMI-1640 (Goding, 1986). The feeder cells were obtained from non-immunized BALB/c mice.

1023 hybrids were obtained. Three clones secreting antibodies against a component in the AF1 fraction were detected by indirect one-site enzyme immunoassay as described above. The hybridomas were cloned by limited dilution and further expanded in culture. One clone (designated 12D2/C6), had a shown strong reactivity by immunoassay and was further expanded using a roller bottle apparatus. The cells were grown in RPMI-1640 supplemented with 20% FCS, 2 mM L-Glutamine, 100 units/ml penicillin, 100 µg/ml streptomycin at 37° C. in a humid atmosphere of 5% $CO_2$ in air for about 40 days with IgG rich media replenished with fresh media every 5-6 days. Two clones designated 14A3 and 21B4 were stored in liquid nitrogen for future investigation.

The recovery of the immunoglobulin purified from culture fluid was determined using an indirect one-site ELISA and the purity by SDS-PAGE. The isotype of the immunoglobulin was determined to be an IgG1 using the mouse antibody isotyping kit.

This monoclonal antibody preparation was used to characterise the corresponding amniotic fluid protein by western blot analysis, and to test the identity of this protein to the original protein purified from amniotic fluid.

The AF1 pools containing the PROM markers were concentrated to 3 mL and individually applied to a pre-calibrated (2.5 cm×75 cm) Sephacyl S-300 column. Similarly, immunoaffinity purified PROM markers was also applied to the same column to estimate its native molecular weight. Serial 2.5 mL fractions were collected and subjected to SDS-PAGE electrophoresis to identify the protein at 75 kDa. Fractions corresponding to a molecular weight range of 300-330 kDa were found to contain the protein giving an estimated native molecular weight of 320 kDa. The sub-unit molecular weight from SDS-PAGE electrophoresis of 75 kDa would be consistent therefore with the native protein composed of multiple subunits.

FIG. 1 shows the results of a western blot analysis (lanes 1-2) following SDS-PAGE electrophoresis in 4-15% gradient gels in the presence of SDS/β-mercaptoethanol. One major band of reactivity is seen and it is identical for the PROM marker purified using an 12D2/C6 immunoaffinity column (lane 1) and in the AF1 fraction applied to the size exclusion column (lane 2). This band corresponds to a sub-unit molecular weight of 75 (+4) kDa (FIG. 1), a mass identical to that of the protein originally purified from amniotic fluid.

EXAMPLE 3

Indirect 1-Site Screening Enzyme Immunoassay

Amniotic fluid samples (n=6 to 10) and maternal blood (plasma or serum; n=6 to 10) obtained from different patients were pooled to provide a final working volume of 50-100 mL. Sample pools were pre-treated with AGB; 1:1 (v/v) for amniotic fluid and 6:1 (v/v) for maternal blood and mixed end-over-end for 4 hours. The solution was centrifuged at 2000 rpm for 20 min and the supernatants collected into fresh 50 mL sterile culture tubes.

In the indirect 1-site enzyme immunoassay procedure, 100 µL of both amniotic fluid (positive control/s) and maternal blood (negative controls; plasma or serum obtained from pregnant women during their second and third trimesters) were applied in columns to a 96-well microtitre plate/s (NUNC Immunoplate: maxisorp) and incubated at room temperature (approx. 25° C.) for 1 hour. Two different pools of each respective fluid were used in the immunoassay procedure on the day. Plates were washed in PBS (LS) and blocked with 200 µL/well PBS (LS)/1.0% ovalbumin for 2 hours at room temperature. Plates were washed 3 times with PBS(LS), and 0.15 mL of supernatant was added to each well; blanks were similarly prepared but using 200 µL/well of culture supernatant prepared from NS-1 cells grown in identical media to those clones being screened. After 2 hours of incubation, plates were washed 3 times with PBS(LS) containing 0.2% (v/v) Tween-20 [PBS(LS)/Tween], 50 µL/well of peroxidase conjugated goat anti-mouse was added to each well and plated incubated for a further one hour at room temperature. After four washes with PBS(LS)/Tween, 100 µL of ABTS solution was added and the reaction allowed to proceed for 30 min. The reaction was stopped with 3.9% oxalic acid (50 µL per well) and the absorbance measured at a wavelength of 405 nm.

Supernatants tested for their monoclonal antibody specificity by immunoassay and which showed an absorbance reading 4-fold greater than both the blank and negative controls were re-tested seven days following the first screening immunoassay using the same format for the assay but with new pools (n=3) of both positive and negative control sera obtained from new patients. Those clones which again presented strong reactivity to the positive controls were re-tested by immunoassay against a further three new pools (positive and negative controls) after a period of seven days. Monoclonal antibodies at this stage which demonstrated specific reactivity to the positive control pools were cloned by limited dilution.

EXAMPLE 4

Purification and Characterisation of Monoclonal Antibody 12D2/C6

A 5 mL Protein-A [AMERSHAM] column (1.5 cm×10 cm) was prepared and equilibrated with 10 column volumes of 500 mM dipotassium phosphate, 25 mM glycine buffer pH 9.1. 500 mL of culture supernatant was applied to the column and the unbound material washed through with 5 column volumes of the same buffer. The immunoglobulin fraction was eluted using 100 mM sodium acetate 3.5 and 5 mL fractions were collected. The purification of immunoglobulin was monitored by SDS-PAGE and an indirect one-site EIA. The antibody was recovered, pooled and stored in 0.5 mL aliquots at −70° C. The immunoglobulin isotype was determined from cell culture supernatant using a commercial mouse antibody isotyping kit [SIGMA].

Electrophoresis was performed on 10 and 12.5% SDS-PAGE gels. Electrophoresis was performed on the Mini Protean II system [BIORAD] for 60 min at 180V. Western blotting was performed according to the method of Towbin (1984) with minor modifications; i.e. the use of 0.3M Tris pH 10.4 containing 10% methanol as the anode buffer; 25 mM Tris, 192 mM glycine, pH 9.4 containing 20% (v/v) methanol as the cathode buffer. Electrophoretic transfer was performed at 120 mA for 90 min using a semi-dry electrophoretic blotting system [Biometra; Fast Blot B33]. Calibration curves for molecular weight estimation were obtained from pre-stained Benchmark standards [GIBCO] similarly transferred to the membrane. Blots were soaked in blocking solution (5% [w/v] milk powder) overnight at room temperature and then washed in 3×10 min consecutive washes in TBS (20 mM Tris, 500 mM NaCl, pH 7.5). The 12D2/C6 MAb was diluted in this same wash buffer (1/100) and added to the blot and left overnight at 4° C. Blots were washed in 4×10 min consecutive washes in the same buffer supplemented with 0.02% Tween-20; at which time goat anti-mouse ALP conjugate (BIORAD) or goat anti-mouse HRPO conjugate (DAKO) were diluted in the same buffer was added to the blot and allowed to incubate for a further 4 hours. Blots were rinsed as before and incubated with peroxidase substrate (0.025 mM DAB [KIMENTEC] prepared in 50 mM Tris-HCl, pH 7.6 containing 0.02% $H_2O_2$) or phosphatase substrate (BCIP/NBT [ICN]) solution for 10-30 min. The reactions were terminated by placing the blot into distilled water.

Isoelectric focusing was performed on the BIORAD mini-IEF system. Gels were prepared from 1% agarose (w/v), 3% sucrose and containing 2% ampholytes of different ranges (BIORAD). Samples consisting of purified AMNI-Protein and IEF standards (BIORAD) were applied to the gel on applicator strips and allowed to adsorb into the gel for 5 minutes. The gel was stained for protein by initially fixing for 30 min using 35% methanol, 13% tricarboxylic acid (ICN), 3.5% sulfosalicylic acid [ICN], then suspended into 95% ethanol for a further 20 min, and finally drying the gel under hot air. The dried gel was placed into a solution of 30% methanol, 10% acetic acid containing Coomassie blue R-250 (SIGMA [0.2% w/v]) for up to 20 min. The gel was then de-stained using 30% methanol, 10% acetic acid until the background was clear.

Only one major band of reactivity against purified protein is evident which corresponds to an isoelectric point of 7.9+ 0.4.

A chromatography column (2.5 cm×100 cm) was packed with Sephacryl S-300 and equilibrated at 11.0 mL/min with 50 mM Tris-HCl (pH 7.4) for 12 hr. Following column equilibration (10 column volumes), gel filtration standards [BIORAD] were run and a standard curve constructed. Amniotic fluid (AF1) post immunoaffinity chromatography was spiked with 1% Dextran Blue-2000 ([Pharmacia]), added to the column and 2 mL fractions collected. Fractions were screened by a 1-site EIA; the native molecular weight was determined from the standard curve for fractions shown positive by the EIA.

Molecular weight separation was also performed using bio-spin columns [Millipore] with a 100 or 300 kD molecular weight cut-off. The devices were centrifuged for 15 min at 2500 g and both the retentate and supernatant retained for analysis.

Fractions reacted positively in the EIA test, corresponded to a molecular weight of approximately 320 kD. No other fractions were found to show reactivity. This native molecular weight corresponded with that found previously, during initial protein purification, and was consistent with monoclonal antibody 12D2/C6 reacting with the polypeptide that was originally purified.

EXAMPLE 5

1 Site Enzyme Immunoassay Protocol

Before use, the plates were washed 3 times in PBS(LS). 10 term amniotic fluids were pooled and serially-diluted ½-¹⁄₁₂₈ with PBS(LS)/Tween to allow the establishment of a standard curve. The PROM marker concentration of the pool was given an arbitrary value of 100 U/L. To perform the assay, samples and standards were applied (100 µL/well) in duplicate and incubated at room temperature for 2 hr. Blanks containing PBS(LS) (100 µL/well) instead of sample, were also included. An amniotic fluid positive control was prepared from 10-15 random term amniotic fluids and run on every plate. After a further three washes in PBS(LS)/Tween, 50 µL of the purified 12D2/C6 MAb diluted in PBS(LS)/Tween or 100 µL of the antibody rich cell culture supernatant was added to each well and incubated at room temperature for 2 hr. After 4 washes with PBS(LS)/Tween, 50 µL goat anti-mouse-HRPO conjugate was added to each well and plated incubated for a further 1 hr. After 4 washes with PBS(LS)/Tween, 100 µL of ABTS solution was allowed to react with the enzyme for up to 2 hr. The reaction was stopped with 3.9% oxalic acid (50 µL per well). Optical densities of samples (OD sample) were measured at a wavelength of 405 nm. Calibration curves were constructed from the amniotic fluid pool after subtraction of blank values (OD blank). The levels of protein in individual specimens and controls were calculated from the standard curve.

Figure 2:
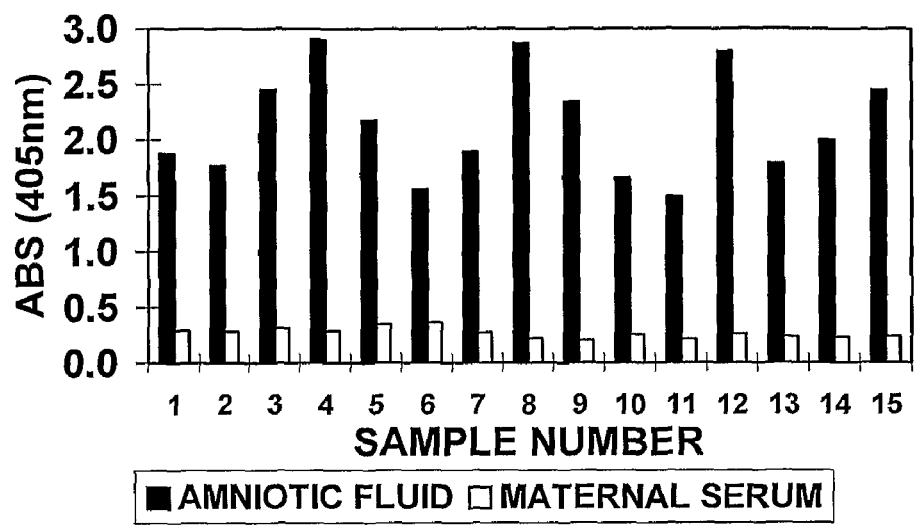
FIG. 2. Results of an indirect 1-site enzyme immunoassay measuring the reactivity of Monoclonal antibody 12D2/C6 to 15 random amniotic fluids (+ve samples) obtained during a caesarean section and 15 random blood sera (−ve samples) obtained from normal pregnant women during their second and third trimesters.

The one-site ELISA procedure was used to evaluate the specificity of the monoclonal antibody 12D2/C6 to amniotic fluid. Amniotic fluids collected at caesarean section were tested against random maternal sera obtained from pregnant women. The results in FIG. 2 show there is strong reactivity to all of the amniotic fluid samples tested and correspondingly no observable reactivity to any of the maternal sera tested. Further testing of maternal blood obtained from women during their trimesters (n=600) by the enzyme immunoassay had also shown no reactivity of the antibody 12D2/C6 to any maternal blood samples tested.

Figure 3:
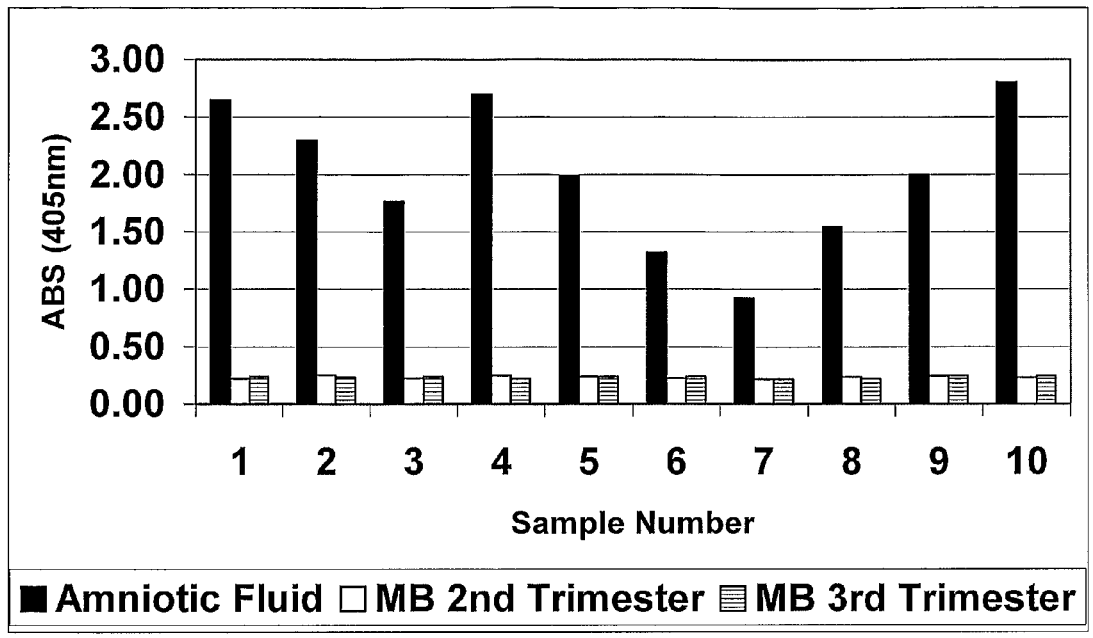
FIG. 3. Results of an indirect 1-site enzyme immunoassay measuring the reactivity of Monoclonal antibody 12D2/C6 to 10 random amniotic fluids collected during CS and random blood sera obtained from 20 different pregnant women (MB) during the second (n=10) and third (n=10) trimesters of pregnancy.

Further testing was performed with a new series of amniotic fluids collected during a caesarean section and tested against a panel of maternal serum obtained from pregnant women during their second and third trimesters. The results of this study (FIG. 3) show that the reactivity is specific to amniotic fluid, and no reactivity was observed to all maternal sera tested.

EXAMPLE 6

Investigation of Mucolytic Agents

To overcome the presence of cervical mucus in the amniotic fluid specimens, a number of agents were investigated in relation to their mucolytic properties. N-acetylcysteine ((NACC) at 0.08, 0.8 and 8% [SIGMA]) and dithiothreitol (DTT) at 0.1, 1 and 5% were prepared in PBS with the pH adjusted to 7.0 with 1M NaOH and 100 mM sodium tetraborate pH 8.4. A pool of term amniotic fluids was mixed with two volumes of the mucolytic agent and allowed to react at room temperature for 5 min. The treated specimen was then assessed by the ELISA.

EXAMPLE 7

Selection of Patients for Establishing PROM Marker Reference Range

To establish the normal reference range, the PROM marker level was measured in post-rupture of the membrane specimens (post-ROM) obtained from the following groups of patients:

a) 68 amniotic fluid specimens were collected at Caesarean Section (CS). These fluids were used in the purification process, in EIA studies including the examination of the effect of the mucolytic agent on the PROM marker and to determine the PROM marker levels in amniotic fluid;

b) 50 amniotic fluid specimens were collected at different trimesters by amniocentesis for various obstetric indications;

c) 38 specimens were collected from women before and after artificial rupture of membranes (ARM), where fluid loss was observed during the procedure. A 0.5-2 mL sample of liquor was aspirated with a syringe or sterile pipette. Eight specimens contained mucus and were used for the mucolytic study.

PROM marker levels were also measured in the sera obtained from 600 pregnant women from all trimesters who had blood samples collected routinely during pregnancy.

A variety of substances were tested for potential interference in the assay procedure by diluting them 1:1 with an amniotic fluid pool. The amniotic fluid pool had a PROM marker level of 44 U/L and gave a level of 22 U/L when diluted 1:1 with 0.8% NACC in sodium tetraborate buffer (Table 1).

TABLE 1

EXAMINATION OF POTENTIAL INTERFERING SUBSTANCES ON THE ACTIVITY OF AMNI-PROTEIN BY 2-SITE EIA

| Interfering Substance | PROM Marker Mean (U/L) | PROM Marker Range (U/L) |
| --- | --- | --- |
| Amniotic Fluid (Control) | 20 | 18-22 |
| Maternal serum (-Alb) | 18 | 16-20 |
| Haemolysed maternal serum | 18 | 16-20 |
| Urine | 19 | 17-21 |
| Tap water | 19 | 16-22 |
| Prostaglandin E2 cream | 19 | 17-21 |
| Cord Blood (-Alb) | 19 | 17-21 |

EXAMPLE 8

2-Site Enzyme Immunoassay

For the 2-site immunoassay, 96-well microtitre plates were activate by the addition of 200 µL per well of 0.2% glutaraldehyde in 100 mM sodium phosphate buffer pH 5.0 for 2 hr. The plates were washed three times in 100 mM sodium phosphate buffer pH 5.0, at which time purified 12D2/C6 was diluted in 50 mM sodium phosphate buffer pH 8.0 at different concentrations and 100 µL added to each well and allowed to incubate at RT for 2 hr. Plates were washed in PBS and blocked with 200 µL per well of 1% ovalbumin (w/v), 0.02% azide and stored at 4° C. for up to seven days prior to use. Before use, plates were washed with PBS (high salt) HS/Tween wash buffer (3.2 mM Na$_2$HPO$_4$, 1.5 mM KH$_2$PO$_4$, 2.7 mM KCl, 0.272M NaCl, pH 7.4 containing 0.5% (v/v) Tween 20).

To perform the assay, samples and standards were applied (100 μL/well) in duplicate and incubated at room temperature for 2 hr. Blanks containing wash buffer were also included. An amniotic fluid control prepared from 15 random term amniotic fluids was run on the test plate. After a further three washes with PBS (HS)/Tween, 50 μL of IgG-HRPO anti-mouse conjugate was added to each well and incubated at room temperature for 1 hr. After four washes with PBS(HS)/Tween, 100 μL of ABTS solution was allowed to react with the enzyme for a designated period of 30 min to 1 hr. The reaction was stopped with 3.9% oxalic acid (50 μL per well). Optical densities of sample (OD sample) were measured at a wavelength of 405 nm.

25 random amniotic fluids collected at CS were pooled for use as an assay standard and was assigned an arbitrary level of 100 U/L PROM marker.

Figure 4:
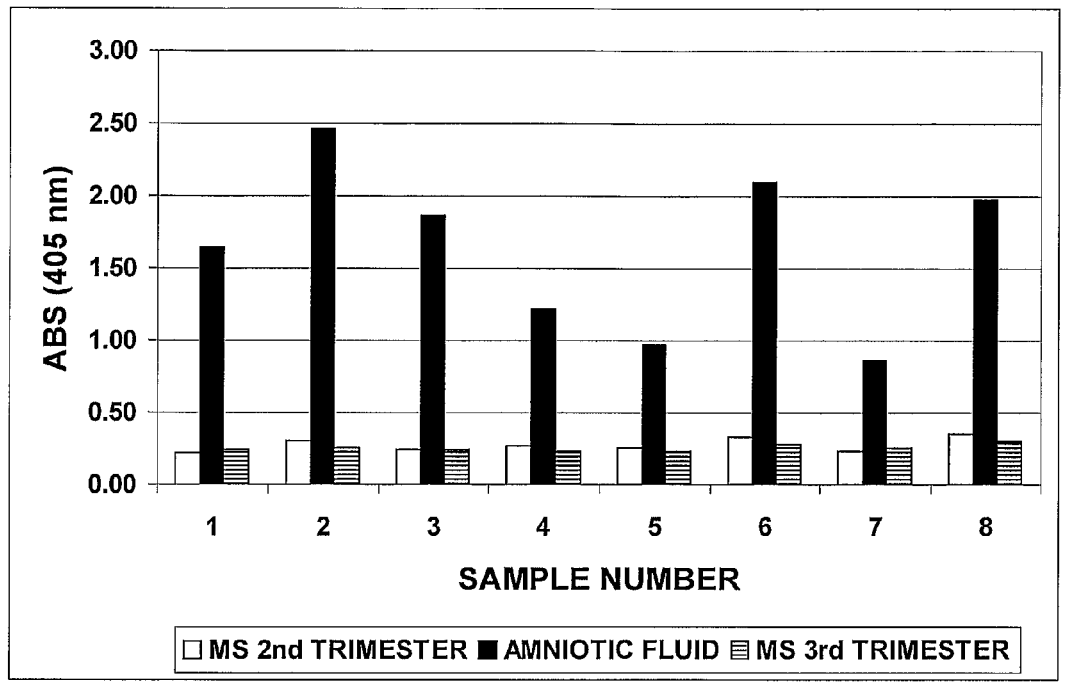
FIG. 4. Results of an indirect 2-site (sandwich) immunoassay measuring the reactivity of 12D2/C6 against a panel of random amniotic fluids collected at CS together with maternal sera obtained from women during their second and third trimesters of pregnancy.

Aliquots of 8 amniotic fluids and maternal sera were applied in an identical fashion to three ELISA plates which were previously coupled with capture antibody at 2.25 μg/well. The results for one of the 2-site ELISA plates are shown in FIG. 4. No reactivity was seen with the maternal sera tested (<10 U/L) whereas all amniotic fluids tested were positive (>10 U/L). On the same plates, the within-run and between-run precision was calculated from the pool analysed 25 times on the same plate, the pool gave a value of 50 (1.7) mean (SD) with a CV of 2%. Similarly, between-run precision was estimated from the pool run 24 times each in three different columns, the pools gave a value of 49.4 (2.0) mean (SD) with a CV of 4%.

Figure 5:
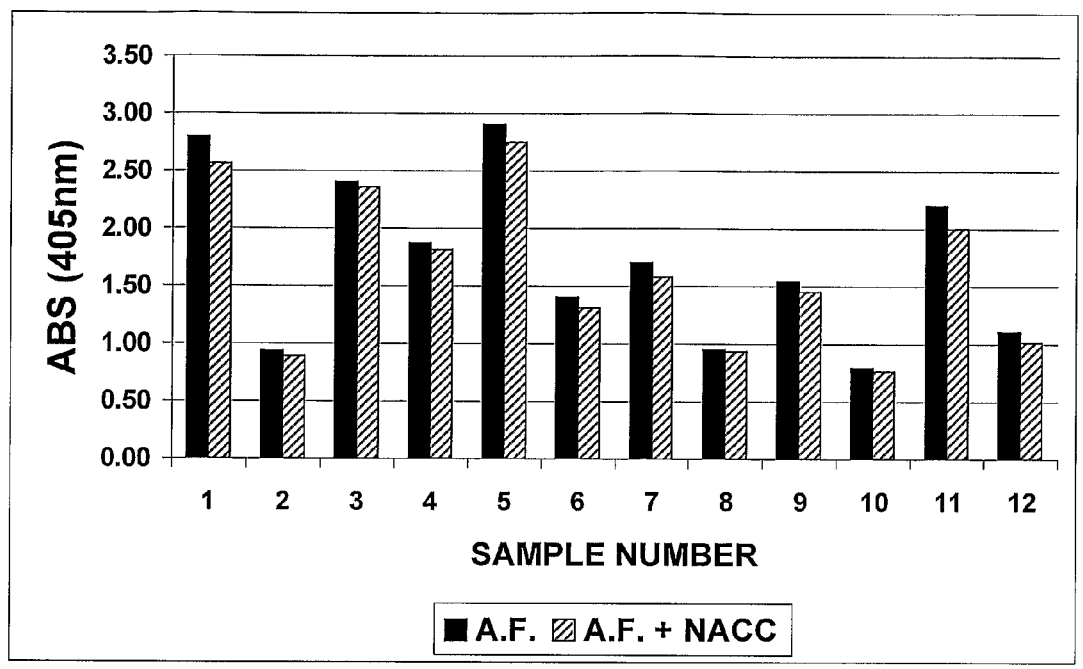
FIG. 5. 2-Site enzyme immunoassay used to examine the effect of pre-incubation with 0.8% N-Acetyl cysteine on AMNI-Protein levels in 12 amniotic fluids.
Figure 6:
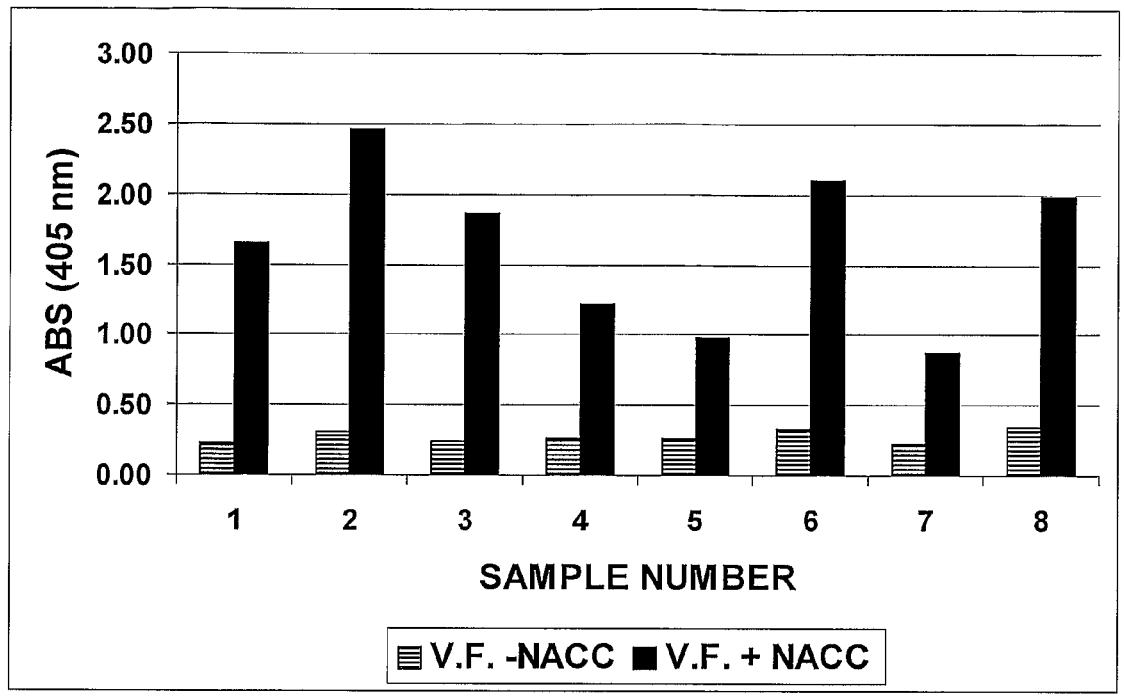
FIG. 6. 2-Site enzyme immunoassay used to examine the effect of pre-incubation with 0.8% NACC on AMNI-Protein levels in eight vaginal fluid specimens containing cervical mucus.
Figure 7:
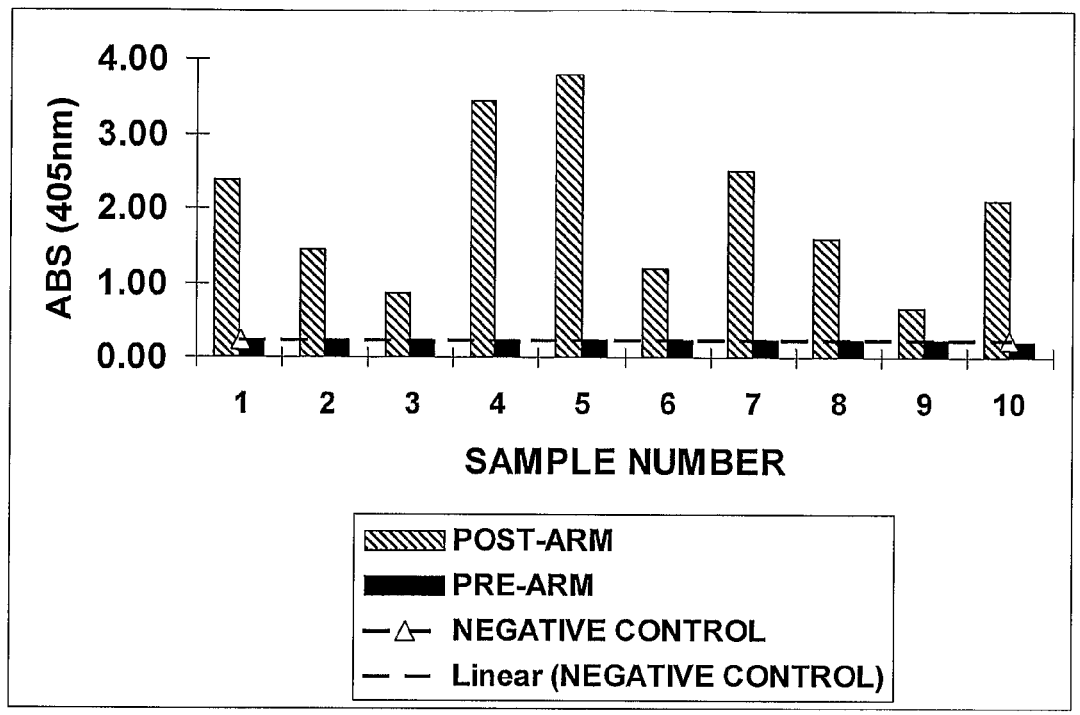
FIG. 7. 2-Site enzyme immunoassay measuring levels of AMNI-Protein in vaginal fluid specimens collected pre- and post-ARM.

Approximately 10% of vaginal fluid specimens collected contained mucus which was difficult to aspirate with a pipette and interfered with the assay by inhibiting PROM marker binding to the capture antibody. To resolve the mucus problem, the inclusion of a mucolytic agent with the test sample and allowing for a 5 minute incubation period prior to testing in the immunoassay was investigated. Of those investigated, NACC (0.8% in 100 mM sodium tetraborate pH 8.4) had little effect on the PROM marker when tested against 12 amniotic fluid samples and the amniotic standard pool collected at CS (FIG. 5). When tested against eight vaginal fluid specimens containing mucus, NACC was active in lysing the mucus as observed by visual inspection, and enabled the detection of the PROM marker by the sandwich immunoassay which had previously given negative results without the NACC treatment (FIG. 6). The specificity of 12D2/C6 within a 2-site assay was further tested against panels of vaginal fluid specimens collected pre- and post ARM were tested. The results as shown in FIG. 7 show reactivity only to the PROM marker present in samples collected post-ARM, no reactivity was observed in any of the pre-ARM specimens as would be expected.

EXAMPLE 9

Sequence Analysis of PROM Marker

Samples for sequencing were mixed 1:1 with tricine sample buffer (10% glycerol (v/v), 2% (v/v) of 20% (w/v) SDS, 0.5% (v/v) 2-mercaptoethanol, 0.002% (w/v) bromophenol blue and 33% (v/v) 3M Tris-HCl [SIGMA], pH 8.45), boiled for 10 min at 100° C. Samples of 10 μL were applied to a 10, 12.5 or 15% homogeneous polyacrylamide gel or within the range of 5-20% gradient polyacrylamide gels all with a 4% stacking gel. Low molecular weight standards [BIORAD, GIBCO] were also run on the same gel. Gels were equilibrated with running buffer; 200 mM Tris pH 8.9 (Anode) and 100 mM Tris, 100 mM Tricine containing 0.1% (w/v) SDS (Cathode).

Electrophoresis was performed on the BIORAD Mini-Protean II system. Proteins were allowed to electrophorese at 180V approximately one hour or until the dye front was near the end of the gel. The gel was placed into the cathode buffer containing 20% (v/v) methanol and allowed to equilibrate for 15 min prior to the blotting procedure. Western blotting was performed using the same buffer formulations as that for the electrophoretic procedure but containing 20% (v/v) methanol. Electrophoretic transfer was performed at 120 mA for 90 min using Semi-Dry Electrophoretic Transfer Cell [BIOMETRA]. Calibration curves for molecular weight estimation were obtained from pre-stained standards [Benchmark: GIBCO] similarly transferred to the membrane.

The membrane was cut into strips which coincided with the PROM marker samples run on the gel. Two strips from the end of the gel were used for blotting and confirmation of the AMNI-Protein by reactivity with 12D2/C6, the remainder of the strips were placed into a sterile Petri dish and stored at −70° C. Blots (membrane strips) were blocked in TBS (200 mM Tris-HCl pH 7.5, 500 mM NaCl) containing 5% milk powder (w/v) for 2 hr at room temperature and then washed in 3×10 min consecutive washes in TBS. Purified 12D2/C6 MAb was diluted in TBS (1/100), added to the blot and left overnight at 4° C. Blots were rinsed as before and anti-mouse alkaline phosphatase labelled conjugate (BIORAD) diluted in the same buffer (1/5000) containing Tween (0.02%) was added to the blot and incubated on a rocking platform for 8 hours. Blots were rinsed in TBS/Tween and incubated with BCIP/NBT substrate (ICN) for 30 min. The reactions were terminated by placing the blot into distilled water.

The claims defining the invention are as follows:

1. A method of diagnosing prolonged rupture of the membranes (PROM) in a pregnant human, which method comprises detecting in a sample of cervicovaginal fluid from the pregnant human the presence or absence of one or more polypeptides of approximately 75 kDa, 20 kDa and 50 kDa as determined by 4-15% gradient SDS-PAGE under reducing conditions, wherein the presence of any combination of said polypeptides comprising at least the polypeptide of approximately 75 kDa indicates PROM in the pregnant human.

2. A method for the detection of polypeptides associated with prolonged rupture of the membranes (PROM) in a pregnant human, which method comprises:
   (i) obtaining a sample of cervicovaginal fluid from said pregnant human;
   (ii) contacting the sample with one or more antibodies, which antibodies are capable of binding specifically to one or more polypeptides of approximately 75 kDa, 20 kDa and 50 kDa as determined by 4-15% gradient SDS-PAGE under reducing conditions, wherein at least one of said antibodies is capable of binding specifically to the polypeptide of approximately 75 kDa, to allow formation of complexes of the antibodies and the polypeptides if present in said sample; and
   (iii) detecting the presence or absence of the antibody-polypeptide complexes in said sample, wherein the presence of any combination of said antibody-polypeptide complexes comprising at least an antibody-polypeptide complex corresponding to the polypeptide of approximately 75 kDa indicates PROM in the pregnant human.

3. The method of claim 1, wherein said sample of cervicovaginal fluid is cervical fluid or vaginal fluid.

4. The method of claim 1, wherein said sample of cervicovaginal fluid is cervical fluid.

5. The method of claim 1, wherein said sample of cervicovaginal fluid is vaginal fluid.

6. The method of claim 2, wherein said sample of cervicovaginal fluid is cervical fluid or vaginal fluid.

7. The method of claim 2, wherein said sample of cervicovaginal fluid is cervical fluid.

8. The method of claim 2, wherein said sample of cervicovaginal fluid is vaginal fluid.

9. The method of claim 2, wherein said sample of cervicovaginal fluid is obtained by a vaginal swab or by collecting vaginal wash using a suitable buffer.

10. The method of claim 1, wherein said sample of cervicovaginal fluid is diluted with suitable buffer or diluent.

11. The method of claim 2, wherein said sample of cervicovaginal fluid is diluted with suitable buffer or diluent.

12. The method of claim 1, wherein said sample of cervicovaginal fluid is mixed with a mucolytic agent before detecting said polypeptides.

13. The method of claim 2, wherein said sample of cervicovaginal fluid is mixed with a mucolytic agent before contacting said sample with said antibodies.

14. The method of claim 1, wherein the detection of the presence or absence of said polypeptides comprises exposing said sample to antibodies that are capable of binding specifically to said polypeptides.

15. The method of claim 1, wherein the detection of the presence or absence of said polypeptides is by enzyme linked immunosorbent assay using antibodies that are capable of binding specifically to said polypeptides.

16. The method of claim 2, wherein the step of contacting the sample with one or more antibodies is by enzyme linked immunosorbent assay.

17. A method of diagnosing prolonged rupture of the membranes (PROM) in a pregnant human, which method comprises detecting in a sample of cervicovaginal fluid from the pregnant human the presence or absence of a polypeptide of approximately 75 kDa as determined by 4-15% gradient SDS-PAGE under reducing conditions, wherein the presence of said polypeptide in said sample indicates PROM in the pregnant human.

18. A method for the detection of polypeptides associated with prolonged rupture of the membranes (PROM) in a pregnant human, which method comprises:
   (i) obtaining a sample of cervicovaginal fluid from said pregnant human;
   (ii) contacting said sample with one or more antibodies, which antibodies are capable of binding specifically to a polypeptide of approximately 75 kDa as determined by 4-15% gradient SDS-PAGE under reducing conditions, which polypeptides are found in amniotic fluid, to allow formation of complexes of the antibodies and the polypeptides if present in said sample; and
   (iii) detecting the presence or absence of antibody-polypeptide complexes, wherein the presence of said antibody-polypeptide complexes in said sample indicates PROM in the pregnant human.

\* \* \* \* \*